(12) United States Patent
Schwab et al.

(10) Patent No.: US 11,253,114 B2
(45) Date of Patent: *Feb. 22, 2022

(54) WASH, CLEAN AND DRY SYSTEM WITH REMOVABLE SPRAY CANISTER DEVICE

(71) Applicant: Whole Bath, LLC, East Chatham, NY (US)

(72) Inventors: Brian Schwab, East Chatham, NY (US); Shao-Yu Peng, Changhua County (TW); Brian Murray, Albany, NY (US)

(73) Assignee: Whole Bath, LLC, East Chatham, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/703,532

(22) Filed: Dec. 4, 2019

(65) Prior Publication Data

US 2020/0178738 A1 Jun. 11, 2020

Related U.S. Application Data

(63) Continuation-in-part of application No. 15/847,594, filed on Dec. 19, 2017, now Pat. No. 10,563,390, and
(Continued)

(51) Int. Cl.
*A47K 10/48* (2006.01)
*A61M 3/02* (2006.01)
(Continued)

(52) U.S. Cl.
CPC .............. *A47K 10/48* (2013.01); *A47K 13/24* (2013.01); *A61M 3/022* (2014.02);
(Continued)

(58) Field of Classification Search
CPC ....... A47K 10/48; A47K 13/24; A61M 3/022; A61M 3/0279; A61M 3/06; A61M 11/08;
(Continued)

(56) References Cited

U.S. PATENT DOCUMENTS 2,875,450 A 3/1959 Umann
D198,085 S 4/1964 Rich
(Continued)

FOREIGN PATENT DOCUMENTS

DE 1625201 2/1970
EM 025022450001 7/2014
(Continued)

OTHER PUBLICATIONS

U.S. Appl. No. 15/847,594, filed Dec. 19, 2019, Brian Schwab.
(Continued)

*Primary Examiner* — Janie M Loeppke
(74) *Attorney, Agent, or Firm* — Michael D. Eisenberg

(57) ABSTRACT

A method and a wash, clean and dry system are provided for washing, cleaning and drying a surface region of a human body. The system includes a toilet seat assembly with a bidet assembly having a spray canister device for spraying the surface region with a solution, such as a skin protecting barrier solution, a cleaning solution or a medicated solution. In one aspect, the spray canister device can be movably insert into and out of the toilet seat assembly and is easy to operate and use. In addition, the bidet assembly further includes a spray nozzle assembly and a drying nozzle assembly, which are adapted to wash, clean and dry the region of the human body in three dimensional moments. The removable spray canister device with the removable sleeved cover element is thus easy to carry and be re-filled with new solutions.

20 Claims, 10 Drawing Sheets

Related U.S. Application Data a continuation-in-part of application No. 15/674,536, filed on Aug. 11, 2017, now Pat. No. 10,982,422, and a continuation-in-part of application No. 15/230,143, filed on Aug. 5, 2016, now abandoned, and a continuation of application No. 15/650,957, filed on Jul. 16, 2017, now Pat. No. 10,869,583, which is a continuation-in-part of application No. 15/649,564, filed on Jul. 13, 2017, and a continuation-in-part of application No. 15/588,637, filed on May 6, 2017, now Pat. No. 10,519,644, and a continuation-in-part of application No. 15/588,638, filed on May 6, 2017, now Pat. No. 10,912,878, and a continuation-in-part of application No. 15/588,640, filed on May 6, 2017, and a continuation-in-part of application No. 15/588,635, filed on May 6, 2017, now Pat. No. 10,526,774.

(60) Provisional application No. 62/373,957, filed on Aug. 11, 2016, provisional application No. 62/363,234, filed on Jul. 16, 2016, provisional application No. 62/363,232, filed on Jul. 16, 2016, provisional application No. 62/333,152, filed on May 6, 2016.

(51) Int. Cl.
    *A47K 13/24* (2006.01)
    *E03D 9/08* (2006.01)
    *B05B 12/00* (2018.01)
    *A61M 3/06* (2006.01)
    *A61M 11/08* (2006.01)
    *B65D 83/14* (2006.01)
    *A61M 15/00* (2006.01)
    *B65D 83/26* (2006.01)
    *B65D 83/38* (2006.01)
    *B05B 15/70* (2018.01)

(52) U.S. Cl.
CPC ............ *A61M 3/0279* (2013.01); *A61M 3/06* (2013.01); *A61M 11/08* (2013.01); *B05B 12/002* (2013.01); *B65D 83/759* (2013.01); *E03D 9/08* (2013.01); *A61M 15/009* (2013.01); *A61M 2205/3561* (2013.01); *A61M 2205/505* (2013.01); *B05B 15/70* (2018.02); *B65D 83/267* (2013.01); *B65D 83/386* (2013.01)

(58) Field of Classification Search
CPC ........ A61M 15/009; A61M 2205/3561; A61M 2205/505; B05B 12/002; B05B 15/70; B65D 83/759; B65D 83/267; B65D 83/386; E03D 9/08

See application file for complete search history.

(56) References Cited

U.S. PATENT DOCUMENTS

| | | |
|---|---|---|
| 3,306,252 A | 2/1967 | Knight |
| 3,516,424 A | 6/1970 | Eagle |
| 3,810,260 A | 5/1974 | Lodi |
| 3,995,326 A | 12/1976 | Umann |
| 4,279,362 A | 7/1981 | Pursell |
| 4,287,618 A | 9/1981 | Silver |
| 4,327,560 A | 5/1982 | Leon |
| D266,758 S | 11/1982 | Johannsen |
| 4,422,189 A | 12/1983 | Couvrette |
| D279,184 S | 6/1985 | Sakamoto |
| 4,628,548 A | 12/1986 | Kurosawa |
| D303,966 S | 10/1989 | Fritzsche |
| 4,903,347 A | 2/1990 | Garcia |
| 4,987,617 A | 1/1991 | Furukawa |
| 5,031,252 A | 7/1991 | Oyama |
| 5,101,520 A | 4/1992 | Lockhart |
| 5,201,080 A | 4/1993 | Tanaka |
| 5,203,037 A | 4/1993 | Kang |
| 5,247,711 A | 9/1993 | Kwon |
| 5,335,855 A | 8/1994 | Borod |
| D355,246 S | 2/1995 | Kawamura |
| 5,409,167 A | 4/1995 | Borod |
| D367,922 S | 3/1996 | Kobayashi |
| 5,504,948 A | 4/1996 | Chandler |
| 5,551,098 A | 9/1996 | Wilk |
| 5,566,402 A | 10/1996 | Agha El-Rifai |
| 5,630,234 A | 5/1997 | Childs |
| D387,851 S | 12/1997 | Pieters |
| 5,720,054 A | 2/1998 | Nakayama |
| 5,765,238 A | 6/1998 | Furukawa |
| 5,813,060 A | 9/1998 | Klopocinski |
| 5,864,894 A | 2/1999 | Fedele |
| 5,898,956 A | 5/1999 | Kurisaki |
| 5,911,516 A | 6/1999 | Chang |
| 5,953,765 A | 9/1999 | Hayashi |
| 5,987,659 A | 11/1999 | Cannizzaro |
| 6,003,159 A | 12/1999 | Sadegh |
| 6,009,570 A | 1/2000 | Hargest |
| D423,655 S | 4/2000 | Otte |
| 6,073,275 A | 6/2000 | Klopocinski |
| 6,105,178 A | 8/2000 | Kurisaki |
| D432,220 S | 10/2000 | Hulsebus |
| 6,128,788 A | 10/2000 | Yamazaki |
| D435,638 S | 12/2000 | Merry |
| 6,167,577 B1 | 1/2001 | Hammad |
| 6,178,568 B1 | 1/2001 | Boulieris |
| 6,192,527 B1 | 2/2001 | Paul |
| D451,076 S | 11/2001 | Sommer |
| D451,177 S | 11/2001 | Scholpp |
| 6,339,852 B1 | 1/2002 | Huang |
| 6,397,406 B1 | 6/2002 | Moshkovich |
| 6,449,780 B1 | 9/2002 | Merry |
| 6,481,590 B1 | 11/2002 | Simkins |
| D471,966 S | 3/2003 | Hatakenaka |
| D481,016 S | 10/2003 | Hillis |
| D485,337 S | 1/2004 | Tani |
| 6,688,500 B1 | 2/2004 | Cheng |
| 6,691,328 B2 | 2/2004 | Delfino |
| 6,754,912 B1 | 6/2004 | Hayashi |
| D500,130 S | 12/2004 | Jung |
| D508,733 S | 8/2005 | Peng |
| D512,425 S | 12/2005 | Watanabe |
| 6,973,679 B1 | 12/2005 | Schad |
| 7,096,518 B2 | 8/2006 | Takenaga |
| D528,991 S | 9/2006 | Katsuyama |
| 7,120,946 B1 | 10/2006 | Lazar |
| 7,127,750 B2 | 10/2006 | Lim |
| D533,788 S | 12/2006 | Kleiman |
| 7,155,755 B2 | 1/2007 | Olivier |
| D538,907 S | 3/2007 | Kaule |
| 7,191,473 B2 | 3/2007 | Matsumoto |
| D541,225 S | 4/2007 | Katsuyama |
| 7,216,374 B2 | 5/2007 | Hassan |
| 7,284,285 B2 | 10/2007 | Scalzi |
| 7,287,286 B2 | 10/2007 | Lee |
| D554,613 S | 11/2007 | Hikino |
| D558,181 S | 12/2007 | Takada |
| D564,976 S | 3/2008 | Billings |
| D565,554 S | 4/2008 | Fan |
| D578,515 S | 10/2008 | Ikeda |
| D579,342 S | 10/2008 | Claughton |
| D583,030 S | 12/2008 | Kobayashi |
| D594,537 S | 6/2009 | Driedger |
| D594,945 S | 6/2009 | Nakasaki |
| 7,543,339 B1 | 6/2009 | Harris |
| D608,426 S | 1/2010 | Ando |
| D616,445 S | 5/2010 | Wong |
| D634,735 S | 3/2011 | Maier |
| D639,399 S | 6/2011 | Takeuchi |
| D639,400 S | 6/2011 | Kang |
| 7,954,181 B2 | 6/2011 | Lim |
| 8,060,953 B1 | 11/2011 | Dorra |
| D654,808 S | 2/2012 | Gidlow |

(56) References Cited

U.S. PATENT DOCUMENTS

| | | |
|---|---|---|
| 8,161,580 B2 | 4/2012 | Hashidume |
| 8,261,377 B2 | 9/2012 | Oh |
| D668,642 S | 10/2012 | Feldman |
| 8,291,527 B2 | 10/2012 | Pan |
| D670,659 S | 11/2012 | Ishikawa |
| D671,935 S | 12/2012 | Mao |
| 8,365,317 B1 | 2/2013 | Dorra |
| 8,425,475 B2 | 4/2013 | Sodo |
| D682,246 S | 5/2013 | Boqueho |
| D688,359 S | 8/2013 | Ogata |
| D692,417 S | 10/2013 | Tu |
| D692,541 S | 10/2013 | Hosoi |
| D698,754 S | 2/2014 | Vuillet |
| D703,797 S | 4/2014 | Shinozaki |
| D704,316 S | 5/2014 | Ishikawa |
| D704,317 S | 5/2014 | Shinozaki |
| D706,402 S | 6/2014 | Yeung |
| D708,954 S | 7/2014 | Barnes |
| 8,776,278 B1 | 7/2014 | Dorra |
| D713,815 S | 9/2014 | Ookawa |
| D715,774 S | 10/2014 | Lee |
| D716,768 S | 11/2014 | Lee |
| D717,930 S | 11/2014 | Kergoet |
| 8,904,575 B1 | 12/2014 | Lindheimer |
| D724,058 S | 3/2015 | Chandel |
| D724,059 S | 3/2015 | Kim |
| 9,049,970 B2 | 6/2015 | Dorra |
| D750,765 S | 3/2016 | Giametta |
| 9,273,454 B2 | 3/2016 | Slawinski |
| 9,279,241 B2 | 3/2016 | Morioka |
| D753,095 S | 4/2016 | Jou |
| 9,464,425 B2 | 10/2016 | Bailey |
| D781,808 S | 3/2017 | Pista |
| D792,867 S | 7/2017 | Maxwell |
| D805,615 S | 12/2017 | Schwab |
| 9,889,982 B2 | 2/2018 | Falcon |
| 2003/0140407 A1 | 7/2003 | Matsumoto |
| 2004/0055080 A1 | 3/2004 | Marshall |
| 2005/0000006 A1 | 1/2005 | Takenaga |
| 2005/0010997 A1 | 1/2005 | Olivier |
| 2006/0000012 A1 | 1/2006 | Schad |
| 2006/0047055 A1 | 3/2006 | Agostini |
| 2006/0265801 A1 | 11/2006 | Riccobon |
| 2007/0241929 A1 | 10/2007 | Marchetto |
| 2008/0055394 A1 | 3/2008 | Shiue |
| 2008/0201837 A1 | 8/2008 | Oh |
| 2008/0251551 A1 | 10/2008 | Huber |
| 2009/0313752 A1 | 12/2009 | Kunimoto |
| 2010/0012685 A1 | 1/2010 | Ramsey |
| 2010/0152475 A1 | 6/2010 | Raichle |
| 2010/0176224 A1 | 7/2010 | Hasselschwert |
| 2011/0132929 A1 | 6/2011 | Bennett |
| 2011/0133001 A1 | 6/2011 | Cooper |
| 2011/0191950 A1 | 8/2011 | Liu |
| 2011/0203044 A1 | 8/2011 | Lim |
| 2012/0005817 A1 | 1/2012 | Jeong |
| 2012/0011647 A1 | 1/2012 | Mochita |
| 2012/0150148 A1 | 6/2012 | Shi |
| 2012/0180785 A1 | 7/2012 | Trill |
| 2012/0266483 A1 | 10/2012 | Palermo |
| 2013/0133131 A1 | 5/2013 | Peng |
| 2013/0180041 A1 | 7/2013 | Ding |
| 2013/0267890 A1 | 10/2013 | Li |
| 2014/0042195 A1 | 2/2014 | Geis |
| 2014/0047626 A1 | 2/2014 | Dorra |
| 2014/0068862 A1 | 3/2014 | Al-Jafar |
| 2014/0107409 A1 | 4/2014 | Bailey |
| 2015/0000025 A1 | 1/2015 | Clements |
| 2015/0059076 A1 | 3/2015 | Tiagai |
| 2015/0203279 A1 | 7/2015 | Falcon |
| 2015/0225167 A1 | 8/2015 | Andersen |
| 2015/0337525 A1 | 11/2015 | Bailey |
| 2016/0316978 A1 | 11/2016 | Peng |
| 2017/0021116 A1 | 1/2017 | Rahmel |
| 2017/0101838 A1 | 4/2017 | Razvi |
| 2017/0142306 A1 | 5/2017 | Peng |
| 2017/0265624 A1 | 9/2017 | Wilson |
| 2017/0319794 A1 | 11/2017 | Schwab |
| 2017/0321406 A1 | 11/2017 | Schwab |
| 2017/0321407 A1 | 11/2017 | Schwab |
| 2017/0321408 A1 | 11/2017 | Schwab |
| 2018/0015238 A1 | 1/2018 | Schwab |
| 2018/0028797 A1 | 2/2018 | Schwab |
| 2018/0036473 A1 | 2/2018 | Schwab |
| 2018/0044903 A1 | 2/2018 | Schwab |
| 2020/0377288 A1* | 12/2020 | Sylvia ............. E03D 9/08 |

FOREIGN PATENT DOCUMENTS

| | | |
|---|---|---|
| EP | 2138640 | 12/2009 |
| FR | 2671294 | 7/1992 |
| FR | 2869596 | 11/2005 |
| GB | 2351779 | 1/2001 |
| IN | 2689190001 | 10/2015 |
| JP | S4815806 | 2/1973 |
| JP | H0893034 | 4/1996 |
| JP | H0988165 | 3/1997 |
| JP | H1163666 | 3/1999 |
| JP | 2001279778 | 10/2001 |
| JP | 2003286738 | 10/2003 |
| JP | 2003342993 | 12/2003 |
| JP | 2007321443 | 12/2007 |
| TW | 469317 | 12/2001 |
| WO | 2008024005 | 2/2008 |
| WO | 2013020240 | 2/2013 |
| WO | 2012044086 | 4/2017 |

OTHER PUBLICATIONS

Extended European Search Report for European Patent Application No. 17831608.9 dated Feb. 25, 2020.

Final Office Action for U.S. Appl. No. 15/588,640 dated Dec. 3, 2018.

Kohler, Self-Cleaning Wand, https://www.youtube.com/watch?v=z629hpdnWj8, published Oct. 12, 2016.

Office Action from Chinese Patent Application No. 2017800570280, with English translation, dated Nov. 27, 2019; 22 pages.

PCT Notification of Transmittal of The International Search Report and The Written Opinion of The International Searching Authority, or Declaration, PCT/US2017/031482, filed on May 6, 2017 by Whole Bath, LLC.

PCT Notification of Transmittal of The International Search Report and The Written Opinion of The International Searching Authority, or Declaration, PCT/US2017/031483, filed on May 6, 2017 by Whole Bath, LLC.

PCT Notification of Transmittal of The International Search Report and The Written Opinion of The International Searching Authority, or Declaration; PCT/US2017/031484, filed on May 6, 2017 by Whole Bath, LLC.

PCT Notification of Transmittal of The International Search Report and The Written Opinion of The International Searching Authority, or Declaration; PCT/US2017/031485, filed on May 6, 2017 by Whole Bath, LLC.

PCT Notification of Transmittal of The International Search Report and The Written Opinion of the International Searching Authority, PCT/2017/031484, dated Aug. 14, 2017.

PCT Notification of Transmittal of The International Search Report and The Written Opinion of The International Searching Authority, PCT/US2016/45932, dated Oct. 24, 2016.

PCT Notification of Transmittal of The International Search Report and The Written Opinion of The International Searching Authority, PCT/US2017/042288, dated Sep. 28, 2017.

PCT Notification of Transmittal of The International Search Report and The Written Opinion of The International Searching Authority, PCT/US2017/42253, dated Nov. 21, 2017.

Schwabcare website 2017, http://schwabcare.com/, site visited Jan. 21, 2018.

(56) References Cited

OTHER PUBLICATIONS

Extended Euorpean Search Report for European Application No. 17831614 dated Mar. 18, 2020.

* cited by examiner

WASH, CLEAN AND DRY SYSTEM WITH REMOVABLE SPRAY CANISTER DEVICE

CROSS REFERENCE TO RELATED APPLICATIONS

This patent application is a continuation of U.S. patent application Ser. No. 15/650,957 which claims benefit of U.S. provisional patent application Ser. No. 62/363,232, filed on Jul. 16, 2016, and U.S. provisional patent application Ser. No. 62/363,234, filed on Jul. 16, 2016, and is a continuation-in-part (CIP) of co-pending U.S. patent application Ser. No. 15/649,564, filed Jul. 13, 2017; a continuation-in-part (CIP) of co-pending U.S. patent application Ser. No. 15/588,635, filed May 6, 2017; a continuation-in-part (CIP) of co-pending U.S. patent application Ser. No. 15/588,637, filed May 6, 2017; a continuation-in-part (CIP) of co-pending U.S. patent application Ser. No. 15/588,638, filed May 6, 2017; and a continuation-in-part (CIP) of co-pending U.S. patent application Ser. No. 15/588,640, filed May 6, 2017. This patent application is a continuation-in-part (CIP) of co-pending U.S. patent application Ser. No. 15/847,594, filed on Dec. 12, 2017, is a continuation-in-part (CIP) of co-pending U.S. patent application Ser. No. 15/230,143 filed on Aug. 5, 2016, and is a continuation-in-part (CIP) of co-pending U.S. patent application Ser. No. 15/674,536 filed on Aug. 11, 2017. The disclosures of all of the above referenced US patent applications are hereby incorporated by reference.

BACKGROUND OF THE INVENTION

Embodiments of the present invention generally relate to a spray device and particularly to a spray canister device for the delivery of water, medication, solutions and/or a pharmaceutical formulation to a surface area of a human subject. More specifically, aspects of the present invention provide a method and a wash, clean and dry system with the spray canister device for washing, cleaning, applying water, medication, and/or a cleaning solution to a region of a human body (e.g., skin, genital or anal area, intimate parts, perineal region) and cleaning thereof.

DESCRIPTION OF THE RELATED ART

Bidets and other modern toilet seat systems have been used to spray water and clean private parts of a user using a toilet. The bidet systems are used for washing the genital and anal areas using cleaning water of appropriate temperature sprayed from the center of the bidet system, instead of a toilet paper after relief stool or urination. Originally being developed for washing the pubic area of females, bidet systems are now popular among people of all ages and both sexes because it is known to be more hygienic to wash the intimate parts and anus with water instead of paper after relief. In addition, cleansing the pubic/anal regions with water may help to avoid infection and prevent hemorrhoids and other anal disease. Furthermore, it is very effective for women with gynecological diseases. It is also very useful for the elderly or obese people to relieve themselves with great convenience.

People who have problems controlling their urine or bowels and suffer from incontinence are at risk of skin problems around the buttocks, hips, genitals, and the area between the pelvis and rectum (perineum). Excess moisture in these areas may result in skin problems (e.g., redness, peeling, irritation, and yeast infections, etc.), and if the person spends most of his or her day in a wheelchair, or bed, it is likely that bedsores may also develop. Such skin problem may be worse if the person uses diapers and other products, which allow urine or stool to be in constant contact with the skin. As such, special care by cleaning and drying the area right away after urinating or having a bowel movement, and/or cleaning the skin with mild, dilute soap and water then rinsing well and gently patting dry.

In addition, moisturizing creams can help keep the skin moist. Also, a skin sealant or moisture barrier, barrier creams or ointments that contain occlusive, barrier-type topical, such as zinc oxide, lanolin, or petrolatum can form a protective barrier on the skin. Some skin care products, often in the form of a spray or a towelette, create a clear, protective film over the skin. A doctor or nurse can recommend barrier creams to help protect the skin. There are a wide variety of ointments, creams, barrier sprays, or lotions known and available in the market for the treatment of diaper rash or incontinence. Most of these products include ingredients that offer some beneficial property to the product, for example, by acting as a skin protectant, water repellant, emollient, neutralizer or antibiotic.

If the individual is alone, applying skin protection paste, ointments, barrier sprays, lotions, solutions, and fluids to an individual's skin is impossible since an individual cannot adequately apply skin protection fluid onto hard-to-reach areas of his or her own back and bottom. Accordingly, it is necessary to utilize the services of a second individual to apply the skin protection fluid on hard-to-reach areas such as the back and upper neck. Thus, there is a need for using a spray device, which applies barrier materials, medicated solutions, fluids, protectants, suspensions, or paste to the skin area of a person, to be incorporated into a bidet seat cleaning system having a water spray nozzle for washing and cleaning private parts of the person.

SUMMARY OF THE INVENTION

The present invention generally provides a method and a wash, dry, clean, and protect system that is easy to handle for washing, drying, and the delivery of water, medication, cleaning solutions, moisturizing creams, skin sealant, moisture barrier, medicaments, and/or a pharmaceutical formulation to a surface area of a human subject. In one embodiment, a wash and dry system is provided and includes a toilet seat assembly, a spray canister device inside a housing of the toilet seat assembly, and a spray nozzle assembly inside the housing of the toilet seat assembly. In another embodiment, the wash and dry system further includes a medicine delivery assembly.

In one aspect, the wash and dry system further includes a dryer assembly. In another aspect, the dryer assembly is able to move back and forth, sideway, and/or rotatably in a three-dimensional direction. In addition, the spray nozzle assembly is able to move back and forth, sideway, and/or rotatably in three-dimensional direction.

In still another aspect, the spray nozzle assembly and the dryer assembly can be combined and formed into a dynamic dryer and spray nozzle assembly. Further, the dynamic dryer and spray nozzle assembly is able to move back and forth, sideway, and/or rotatably in three-dimensional direction.

In another embodiment, the spray canister device of the wash and dry system may include a sleeved cover element and a canister element. In one example, the spray canister device is removable and can be installed in and out of the housing of the wash and dry system though a cover on the housing of the toilet seat assembly. In one aspect, the spray canister device is a stand-alone device for spraying a barrier material or medicament or a solution on to a surface area of a human subject. In another aspect, the sleeved cover element of the spray canister device can be separated from the canister element.

In one example, the sleeved cover element of the spray canister device comprises an opening, a sleeve portion, and a trigger bar. In addition, the sleeved cover element may include a handle grip for easy gripping and easy handling of the spray canister device. In another example, the canister element of the spray canister device includes a top outlet, a bottom portion, and a canister body.

In still another embodiment, the interior content of the canister element is sprayed out of the spray canister device by triggering the trigger bar of the sleeved cover element against the canister element and moving the bottom portion of the canister element to be closer to the opening of the sleeved cover element.

Another embodiment of the invention provides a method for using a wash and dry system. The method includes positioning a wash and dry system near a surface area of a subject, where the wash and dry system includes a toilet seat assembly comprising a housing, a spray canister device inside the housing, and a spray nozzle assembly inside the housing. The method further includes washing the surface area of the subject using the spray nozzle assembly, and applying a spray delivered from an opening of the spray canister device onto the surface area of the subject.

In one aspect, the method further includes, optionally, cleaning the surface area of the subject using a cleaning solution sprayed from the wash and dry system. In another aspect, the method further includes drying the surface area of the subject using a dryer assembly of the wash and dry system.

In one example, drying the surface area is performed by the dryer assembly at high power prior to applying the spray delivered from the spray canister device. In another example, drying the surface area is performed by the dryer assembly at low power after applying the spray delivered from the spray canister device.

Further, the method may also include installing the spray canister device into the housing of the toilet seat assembly prior to using the wash and dry system. In one example, the spray canister device is installed by gripping a handle grip of the spray canister device and positioning the spray canister device into a cover of the housing of the toilet seat assembly. In another example, the spray canister device is installed by coupling a trigger bar of the spray canister device securely onto a delivery rack inside the housing of the toilet seat assembly.

In another embodiment, the method may further include shaking the spray canister device by moving the spray canister device inside the housing of the toilet seat assembly. In one aspect, shaking the spray canister device is performed prior to applying the spray delivered from the spray canister device.

In still another embodiment, the method may further include applying the spray by moving a canister element of the spray canister device against a sleeved cover element of the spray canister device along a delivery rack inside the housing of the toilet seat assembly.

In one embodiment, the removable sleeved cover element of the spray canister device includes a top cap portion, an opening, a sleeve portion, a handle grip, and a trigger bar. In another embodiment, the inner canister element includes a top outlet and a canister body. In still another embodiment, the canister body of the inner canister element is covered by a sleeved portion of the removable sleeved cover element and the top outlet is fitted to channels inside the top cap portion of the removable sleeved cover.

In a further embodiment, a spray canister device is incorporated into a wash, clean and dry bidet system that is designed to easily dispense water, medication, cleaning solutions, moisturizing creams, skin sealant, moisture barrier, medicaments, and/or a pharmaceutical formulation from a wash, clean and dry bidet system to a surface area of a human subject.

The wash and dry system of the present invention applies barrier materials, skin protection lotions and oils, medicaments directly to the skin and an operator of the wash and dry system will be able to spray lotions evenly on the individual, especially in hard-to-reach areas such as the bottom, back and neck of a human subject.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

The present invention includes a method and a wash, dry, clean, and protect system for providing easy washing, cleaning and protection of a person's bottom while using a toilet is provided. In one embodiment, the system can be placed directly over a rim of a toilet bowl or a seat of a toilet seat system. In another embodiment, the wash, dry, clean, and protect system include a removable spray canister device for the delivery of water, medication, cleaning solutions, moisturizing creams, skin sealant, moisture barrier, medicaments, and/or a pharmaceutical formulation to a surface area of a human subject.

The spray canister device as described herein is easy-to-handle and makes it easy to apply and spray fluids, solutions, suspensions, or paste of a barrier chemical or medicament to the skin area of a person. The spray canister device contains a removable sleeved cover element and a canister element to allow for easy operation and make it easy to spray, and can be handled manually or can function together with a toilet seat wash and dry system or other devices.

In one embodiment, a spray canister device is incorporated into a wash, clean and dry bidet system and is designed to easily dispense water, medication, cleaning solutions, moisturizing creams, skin sealant, moisture barrier, medicaments, and/or a pharmaceutical formulation from a wash, clean and dry bidet system to a surface area of a human subject.

Figure 1:
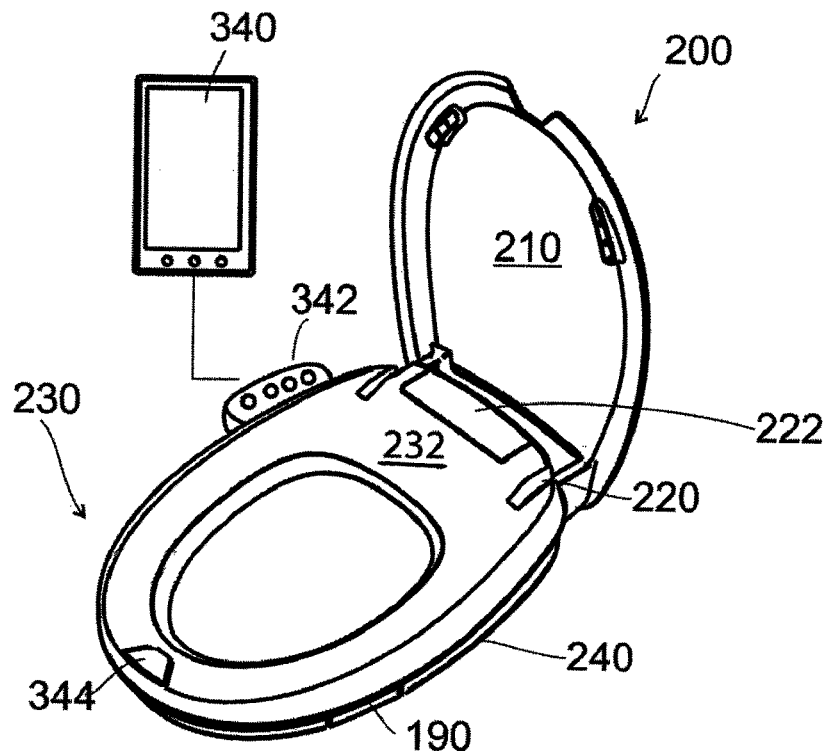
FIG. 1 is a perspective view of a wash and dry system with a spray canister device therein according to one embodiment of the invention.

FIG. 1 is a perspective view of a wash and dry system with a spray canister device 100 (shown in FIG. 2B) according to one embodiment of the invention. In one embodiment, the wash and dry system includes a toilet seat assembly 200 with the spray canister device 100 positioned stationery or removably inside a base housing 220 of the toilet seat assembly 200. In general, the toilet seat assembly 200 includes a seat cover 210, the base housing 220, a base housing cover 222, a seat 230, a seat body 232, and a base 240.

In one example, the wash and dry system further includes a dryer assembly 170 (shown in FIG. 4D) and a spray nozzle assembly 160 (shown in FIG. 4D) positioned inside the base housing 220 of the toilet seat assembly 200. The dryer assembly 170 is able to move back and forth, sideways, and/or rotatably in a three-dimensional direction. In addition, the spray nozzle assembly 160 is able to move back and forth, sideway, and/or rotatably in a three-dimensional direction. In another example, the dryer assembly 170 and the spray nozzle assembly 160 are combined and formed into a dynamic dryer and spray nozzle assembly, such as a wash and dry assembly 150, as shown in FIG. 4D. In one aspect, the dynamic dryer and spray nozzle assembly is able to move back and forth, sideway, and/or rotatably in three-dimensional direction.

The wash and dry system of the present invention applies barrier materials, skin protection lotions and oils, and medicaments directly to the skin and an operator of the wash and dry system will be able to spray lotions evenly on the individual, especially in hard-to-reach areas such as the bottom, back and neck of a human subject.

In addition, the wash and dry system may further include a power switch, a power indicator for powering up the system and operating wash, clean, dry, protect, and/or other functions of the system. In one aspect, the system is connected to a power cord. In another aspect, the system is connected to a battery power pack.

Figure 2A:
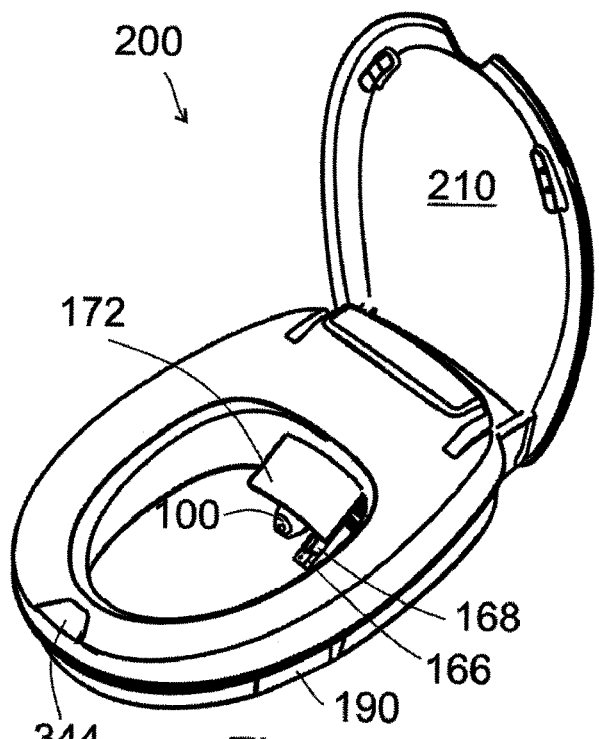
FIG. 2A is a perspective view of a wash and dry system with a spray canister device and a combined dynamic dryer and spray nozzle assembly extended out below a cover according to another embodiment of the invention.

FIG. 2A is a perspective view of one example of a wash and dry system. The wash and dry system may include the spray canister device 100 and a combined dynamic dryer and spray nozzle assembly (e.g., the wash and dry assembly 150, as shown in FIG. 4D). As shown in FIG. 2A, the spray canister device 100 and the wash and dry assembly 150 are adapted to be extended out below a cover 172, which is located near a side of the base housing 220 of the base 240.

Figure 2B:
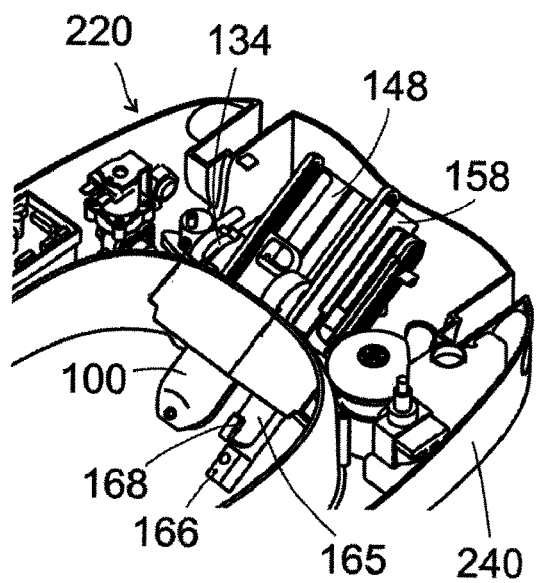
FIG. 2B is an inside view of a housing of a wash and dry system showing a spray canister device and a combined dynamic dryer and spray nozzle assembly extended from a housing of the wash and dry system and extended out below a cover of the base of the wash and dry system according to another embodiment of the invention.

FIG. 2B is an inside view of the base housing 220 of the wash and dry system having the spray canister device 100 and the wash and dry assembly 150 (shown in FIG. 4D) extended from the base housing 220 of the wash and dry system and extended out below the cover 172 of the base 240 of the wash and dry system according to another embodiment of the invention. In one embodiment, the wash and dry assembly 150 is adapted to be connected to a water inlet of a water hose assembly for supplying water and other liquid into the wash and dry system.

Figure 3:
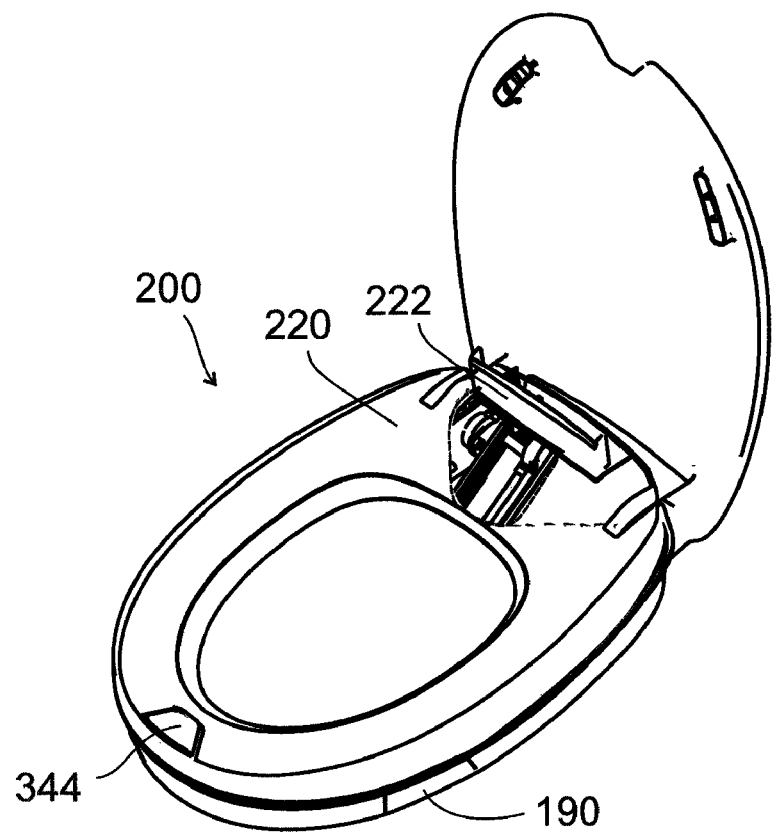
FIG. 3 is a perspective view of a wash and dry system wherein a cover positioned on a housing of a base of the wash and dry system is opened with a spray canister device stored therein according to another embodiment of the invention.

FIG. 3 is a perspective view of a wash and dry system where the base housing cover 222 positioned on the base housing 220 of the base 240 of the wash and dry system is opened with the spray canister device 100 stored therein. In one aspect, the spray canister device is adapted to be removable in and out of the base housing cover 222 of toilet seat assembly 200 of the wash and dry system.

In one embodiment, the wash and dry system further includes a medicine delivery assembly 190. The medicine delivery assembly 190 may include medication and/or cleaner solutions therein. Suitable medication and cleaning solutions are not limited and can be any of a desirable cleaning solution, a medication solution, a fragrant solution, a deodorant solution, a moisturizing solution, and/or combination thereof. In addition, the content of liquid solutions within the medicine delivery assembly 190 can be changeable according to personal preference of a user or under the instruction of a doctor for treating various perineal or urinary tract infections, vaginal infections, and/or hemorrhoids, among others.

Figure 4A:
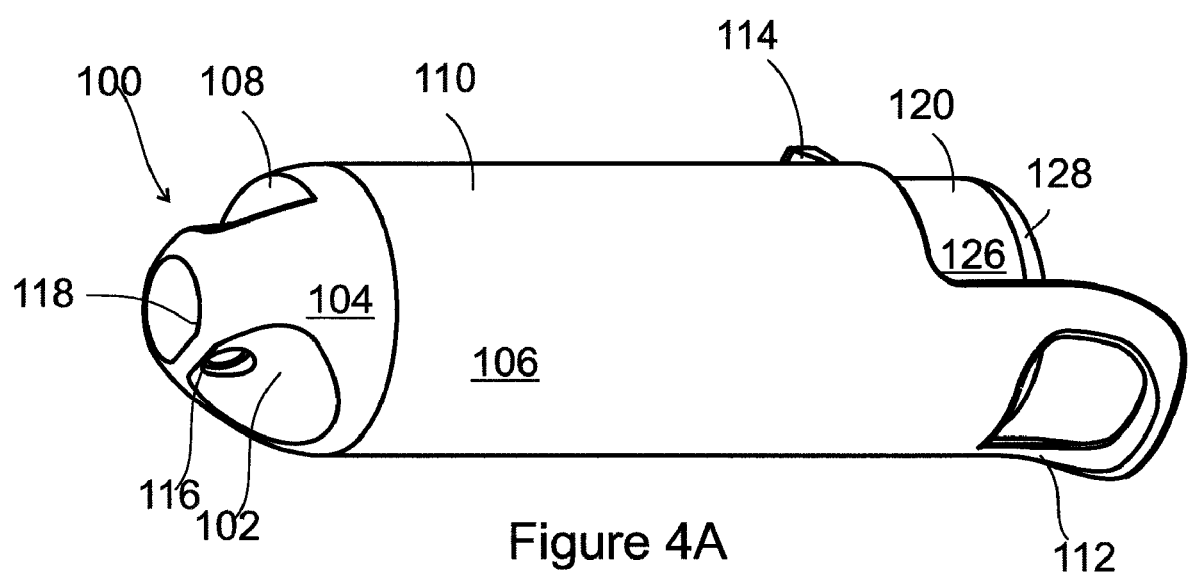
FIG. 4A is a perspective view of a spray canister device with a removable sleeved cover element and a canister element according to another embodiment of the invention.

FIG. 4A is a perspective view of the spray canister device 100. In one aspect, the spray canister device 100 includes a sleeved cover element 110 and a canister element 120 according to another embodiment of the invention. In another aspect, the sleeved cover element 110 of the spray canister device 100 can be removably separated from the canister element 120. In one example, the spray canister device 100 is a stand-alone device for spraying a barrier material or medicament or a solution on to a surface area of a human subject. In another example, the spray canister device 100 is installed into the base housing 220 of the toilet seat assembly 200 through the base housing cover 222 so as to effect spraying a barrier material or medicament or a solution on to a surface area of a human subject. In another example, the sleeved cover element 110 of the spray canister device 100 can be separated from the canister element 120.

As shown in FIG. 4A, the sleeved cover element 110 of the spray canister device 100 includes a top cap portion 104, and a sleeved portion 106. The top cap portion 104 may also include a cut-out portion 102, a top body portion 108, an opening 116, and a top flat surface portion 118. The sleeved portion 107 of the sleeved cover element 110 may also include a handle grip 112 and a trigger bar 114. The handle grip 112 of the sleeved cover element 110 is provided for easy gripping and easy handling of the spray canister device 100. In addition, the canister element 120 of the spray canister device 100 includes a top outlet, a bottom portion 128, and a canister body 126.

Figure 4B:
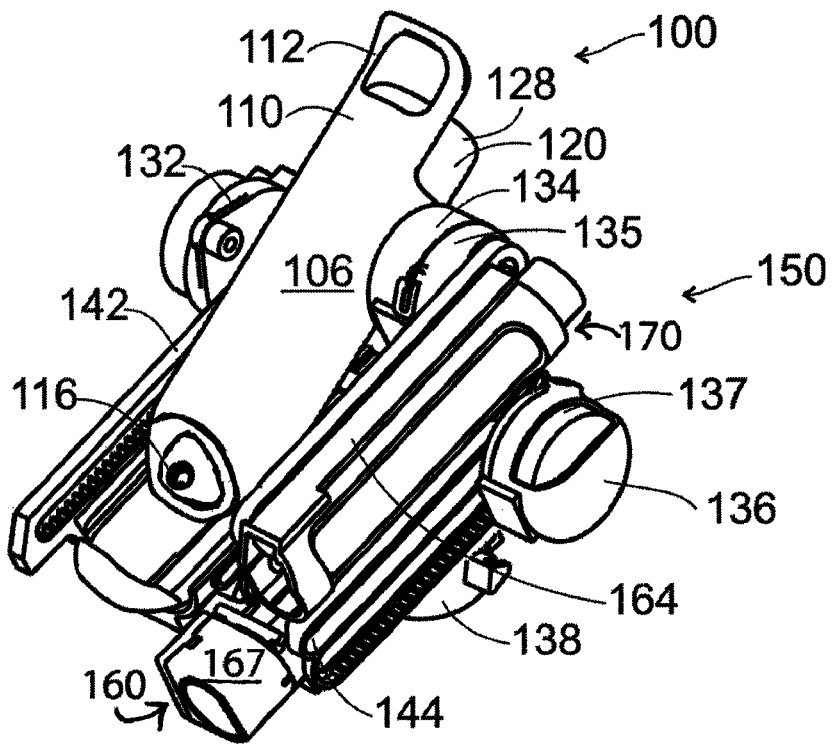
FIG. 4B is a perspective view of operating a spray canister device to fit into a delivery track positioned next to a spray nozzle assembly and a dryer assembly that are combined and formed into a dynamic dryer and spray nozzle assembly according to yet another embodiment of the invention.
Figure 4C:
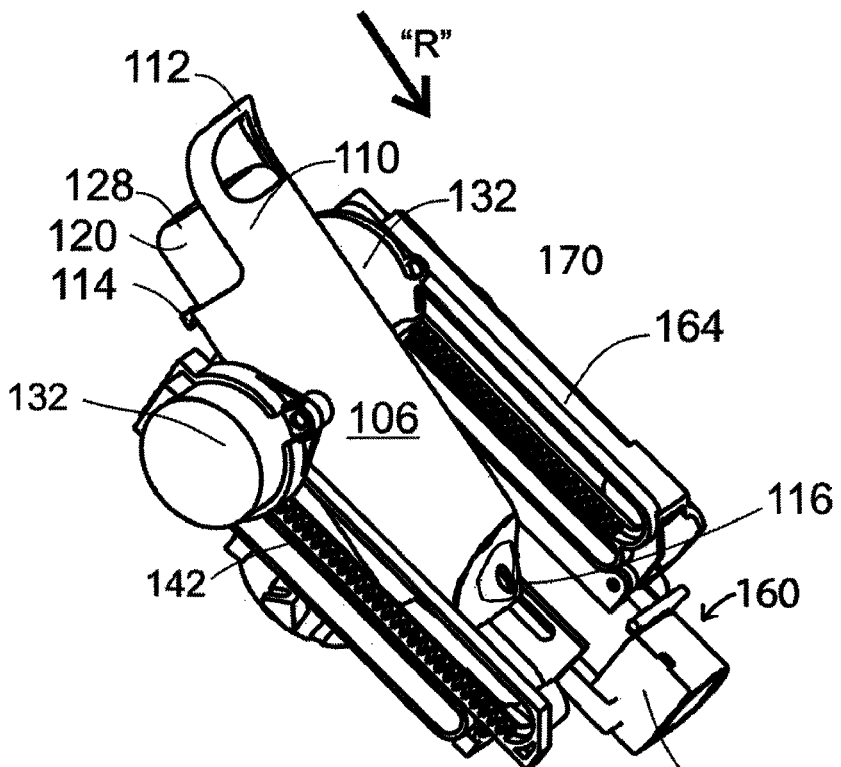
FIG. 4C is another side perspective view of installing the spray canister device of FIG. 4B to be secured onto a delivery track positioned next to a dynamic dryer and spray nozzle assembly according to yet another embodiment of the invention.
Figure 4D:
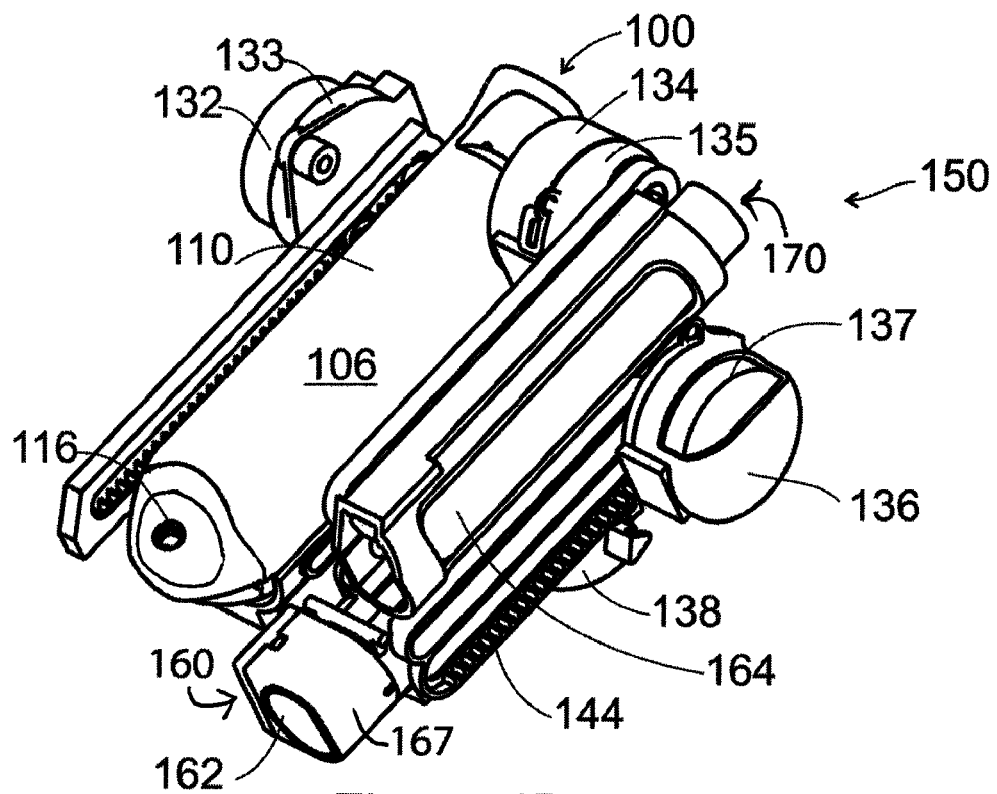
FIG. 4D is another side perspective view of the spray canister device of FIG. 4B when the spray canister device is securely installed onto a delivery track positioned next to a dynamic dryer and spray nozzle assembly according to yet another embodiment of the invention.
Figure 4E:
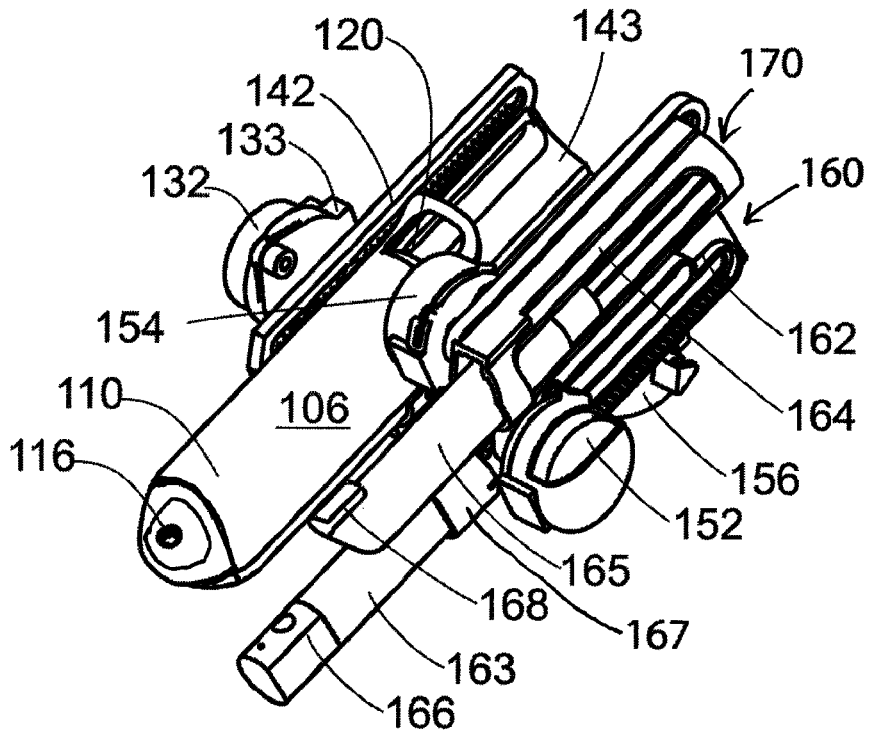
FIG. 4E is another side perspective view of the spray canister device of FIG. 4B after the spray canister device is securely installed next to a dynamic dryer and spray nozzle assembly and both the spray canister device and one or more nozzles head elements of the combined dynamic dryer and spray nozzle assembly is ready to be extended out according to yet another embodiment of the invention.

FIG. 4B is a perspective view of operating and installing the spray canister device 100 to fit into a track 143 positioned next to the wash and dry assembly 150. FIG. 4C is another side perspective view of installing the spray canister device 100 of FIG. 4B to be secured onto the track 143. FIG. 4D is another side perspective view of the spray canister device 100 of FIG. 4B when the spray canister device 100 is securely installed onto a delivery track positioned next to the wash and dry assembly 150. FIG. 4E is another side perspective view of the spray canister device of FIG. 4B after the spray canister device 100 is securely installed next to the wash and dry assembly 150 and both the spray canister device 100 and one or more nozzles head elements of the wash and dry assembly 150 is ready to be extended out.

In one embodiment, the interior content of the canister element 120 is sprayed out of the spray canister device 100 by triggering the trigger bar 114 of the sleeved cover element 110 against the canister element 120 and moving the bottom portion 128 of the canister element 120 to be closer to the opening 116 of the sleeved cover element 110.

Figure 5A:
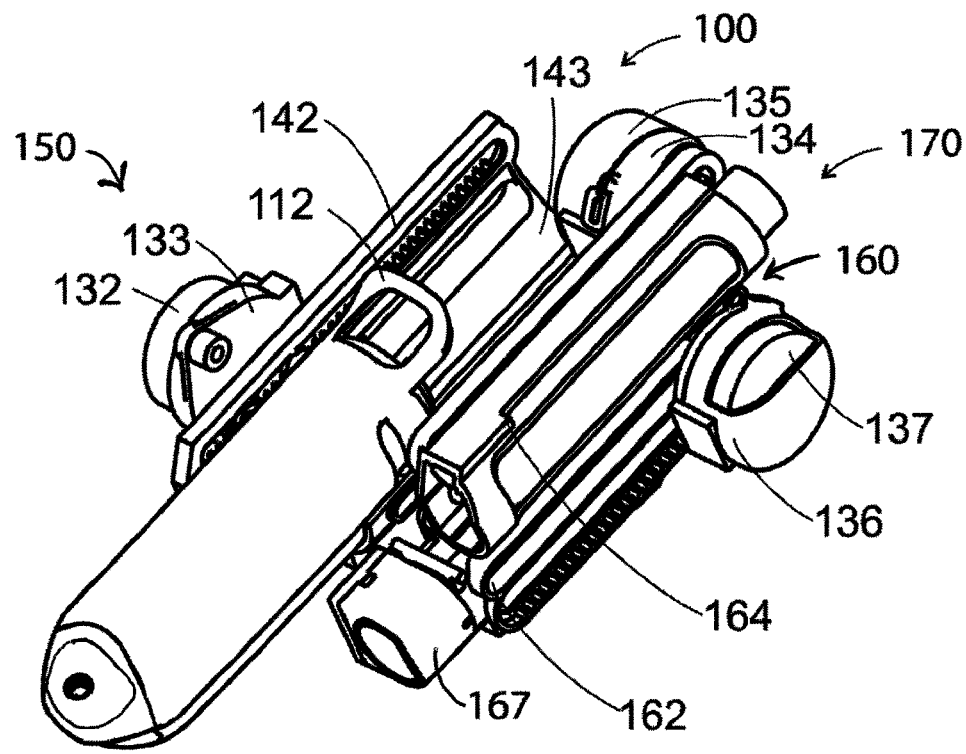
FIG. 5A is another side perspective view of the spray canister device, showing the spray canister device is being extended out and ready to spray a solution out of its front opening according to yet another embodiment of the invention.
Figure 5B:
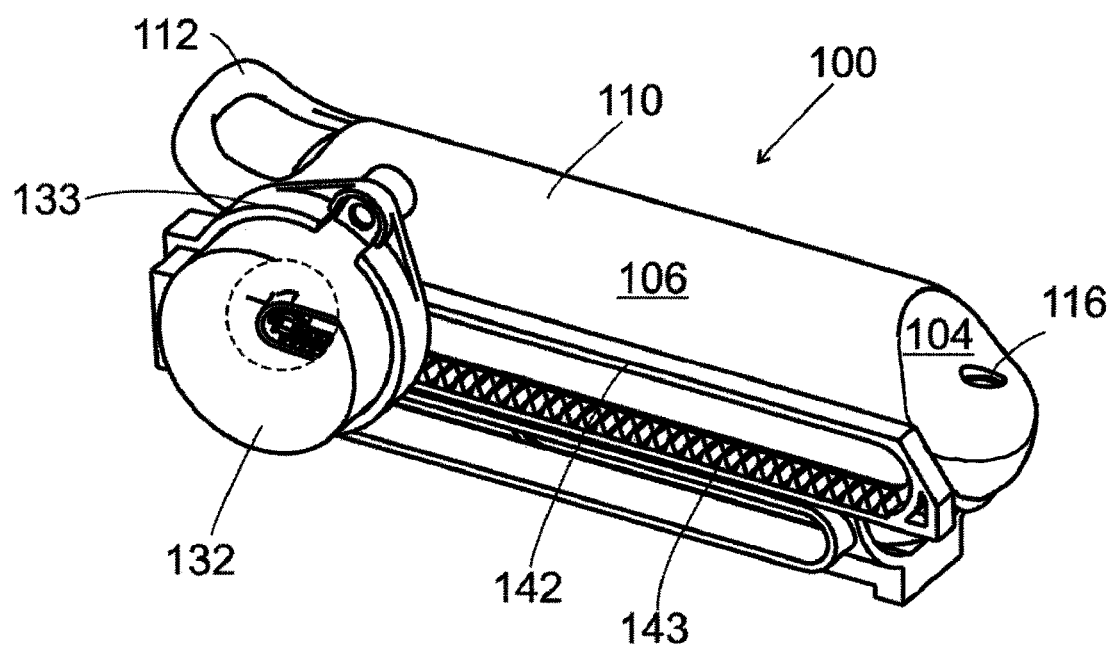
FIG. 5B is a side view of one example of a spray canister device, showing a motor, a rail and a slot element of a driving motor assembly for moving the spray canister device according to one embodiment of the invention.

FIG. 5A is another side perspective view of the spray canister device 100, showing the spray canister device 100 is being extended out and ready to spray a solution out of the opening 116. FIG. 5B is a side view of the spray canister device 100, showing a motor 132, a motor holder 133, a track 143, and a slot element 142 of a driving motor assembly for moving the spray canister device 100.

Figure 5C:
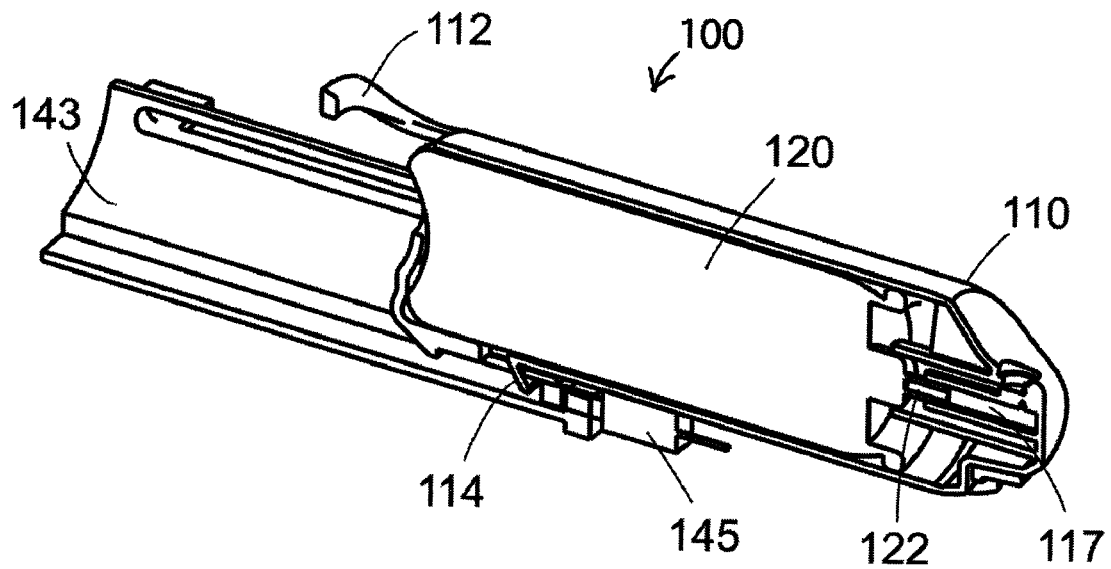
FIG. 5C is a cross-sectional view of the spray canister device of FIG. 5B, showing a driving motor assembly used to move and extend the spray canister device according to one embodiment of the invention.

FIG. 5C is a cross-sectional view of the spray canister device 100 of FIG. 5B, showing the track 143, a solenoid 145 of a driving motor assembly used to couple with the trigger bar 114 of the spray canister device 100 so as to move and extend the spray canister device 100.

Figure 6A:
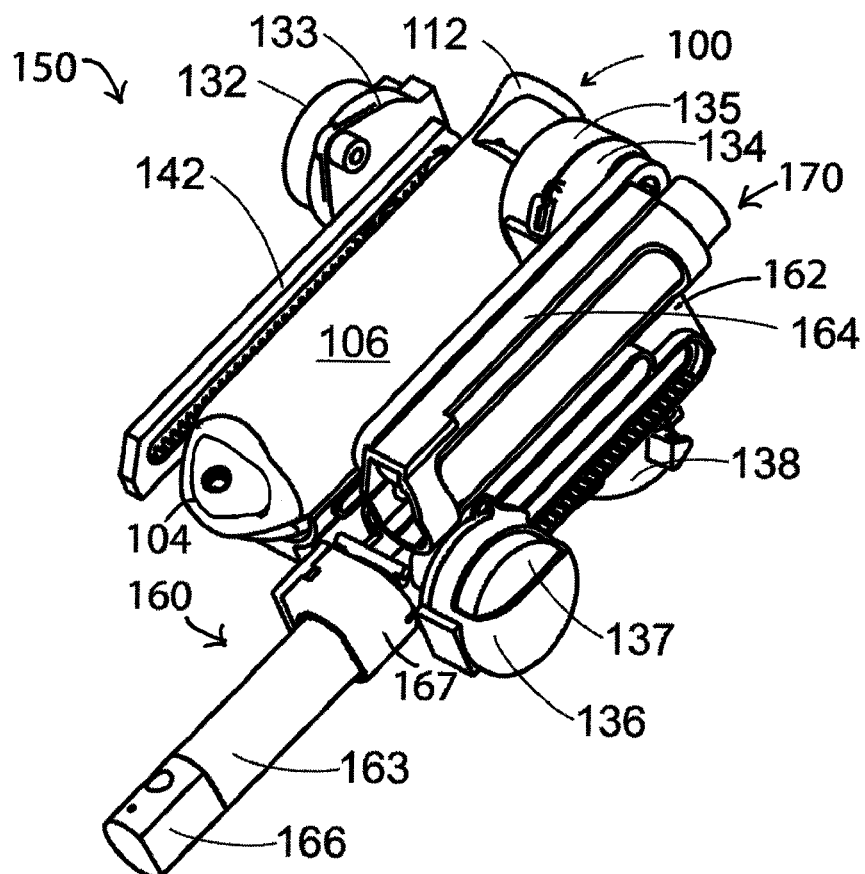
FIG. 6A is a side perspective view of a spray canister device installed next to a dynamic dryer and spray nozzle assembly, showing a spray nozzle wand of the dynamic dryer and spray nozzle assembly is being extended out of a spray nozzle housing and ready to spray water or a cleaning solution out of its front spray nozzle head according to yet another embodiment of the invention.

FIG. 6A is a side perspective view of the spray canister device 100 installed next to the wash and dry assembly 150, showing a spray nozzle wand 163 of the wash and dry assembly 150 is being extended out of a spray nozzle housing 162 and ready to spray water or a cleaning solution out of a spray nozzle head 166.

Figure 6B:
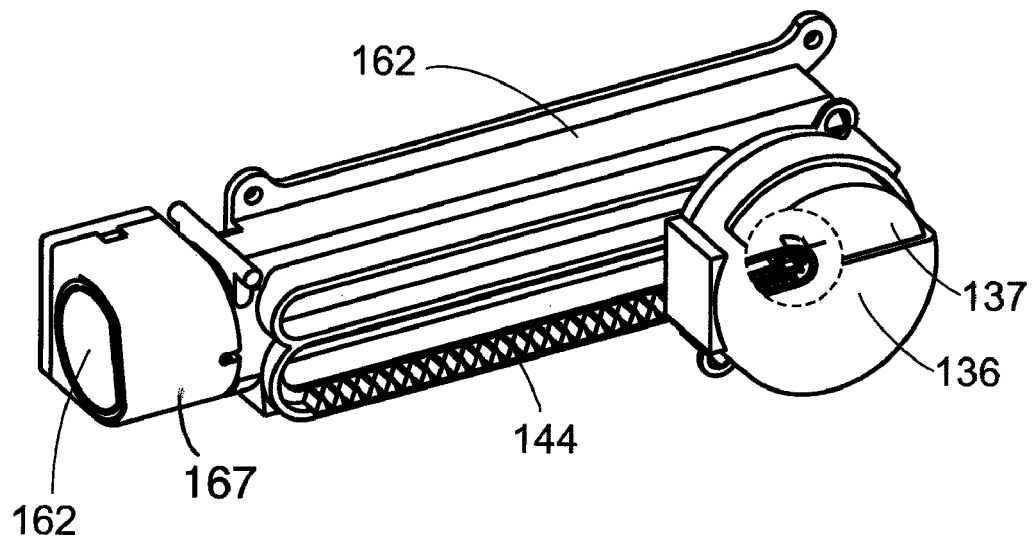
FIG. 6B is a side view of one example of a spray nozzle assembly, showing a spray nozzle housing of the spray nozzle assembly and a driving motor assembly with a motor, a rail and a slot element for moving the spray nozzle assembly according to one embodiment of the invention.

FIG. 6B is a side view of a spray nozzle assembly of the wash and dry assembly 150, showing the spray nozzle housing 162 of the spray nozzle assembly and a driving motor assembly with a motor 136, a motor holder 137, a rack 144 and a slot element for moving the spray nozzle assembly according to one embodiment of the invention.

Figure 6C:
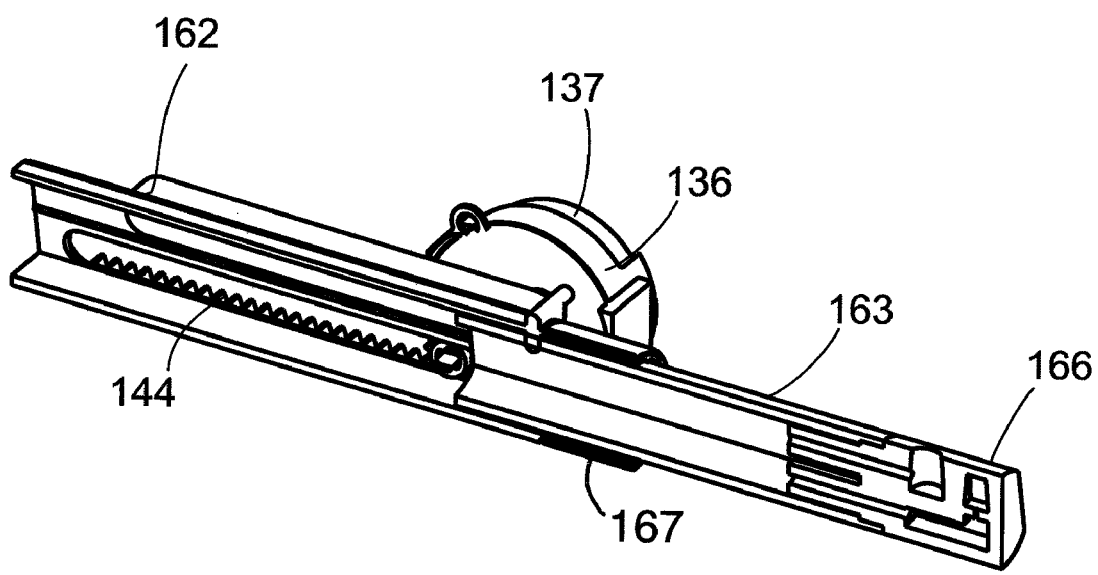
FIG. 6C is a cross-sectional view of the spray nozzle assembly of FIG. 6A, showing a driving motor assembly used to move and extend the spray nozzle assembly according to one embodiment of the invention.

FIG. 6C is a cross-sectional view of the spray nozzle assembly of FIG. 6B, showing the motor 136, the motor holder 137, and the rack 144 of the driving motor assembly used to move and extend the spray nozzle assembly.

As shown in FIGS. 6A-6C, the spray nozzle assembly of the wash and dry system includes the spray nozzle wand 163 and the spray nozzle head 166 that are able to be movably extended by the motor 136 of a driving motor assembly. The spray nozzle assembly further includes one or more liquid channels therein such that the liquids flowing therein can be delivered via the spray nozzle wand 163 and the spray nozzle head 166 and sprayed out. For example, water and other liquids can be sprayed out and used to wash onto a desirable area (e.g., a genital area, an anal area, anterior private parts, perineal region, etc.) of a human body while a human is using a toilet.

The spray nozzle head 166 is adapted to spray out liquid in a stream or a mist form onto a desirable area of a human body. The shape and size of the spray nozzle head 166 positioned at the tip of the spray nozzle wand 163 is not limited and can be a small opening, a multiple-holed nozzle type element, among others.

Suitable liquid that can be contained and flowed within the one or more channels of the spray nozzle assembly of the wash and dry assembly 150 includes water, medication solutions, cleaning solutions and combinations thereof. The temperature of the liquids are not limited and may range from cold water temperature to warm temperature of about 60° C. In one embodiment, the wash and clean system includes a water inlet adapted to connect to a water hose assembly (for supplying water and other liquid into the wash and dry system. For example, the water inlet can be positioned near the back wall of the toilet seat assembly 200.

Figure 7A:
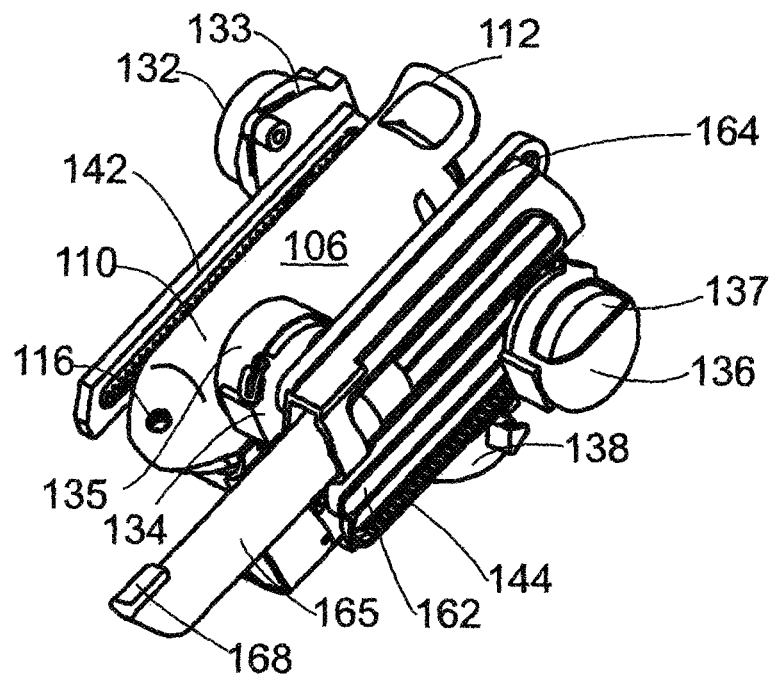
FIG. 7A is a side perspective view of a spray canister device installed next to a dynamic dryer and spray nozzle assembly, showing a dryer wand of the dynamic dryer and spray nozzle assembly extended out of a dryer housing and ready to blow air or gases out of its front blower head according to yet another embodiment of the invention.
Figure 7B:
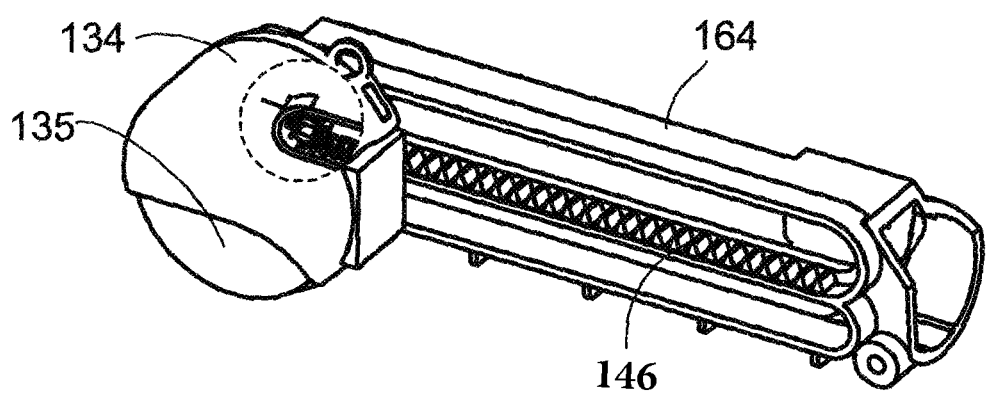
FIG. 7B is a side view of one example of a dryer assembly, showing a dryer housing of the dryer assembly and a driving motor assembly with a motor, a rail and a slot element for moving the dryer assembly according to one embodiment of the invention.
Figure 7C:
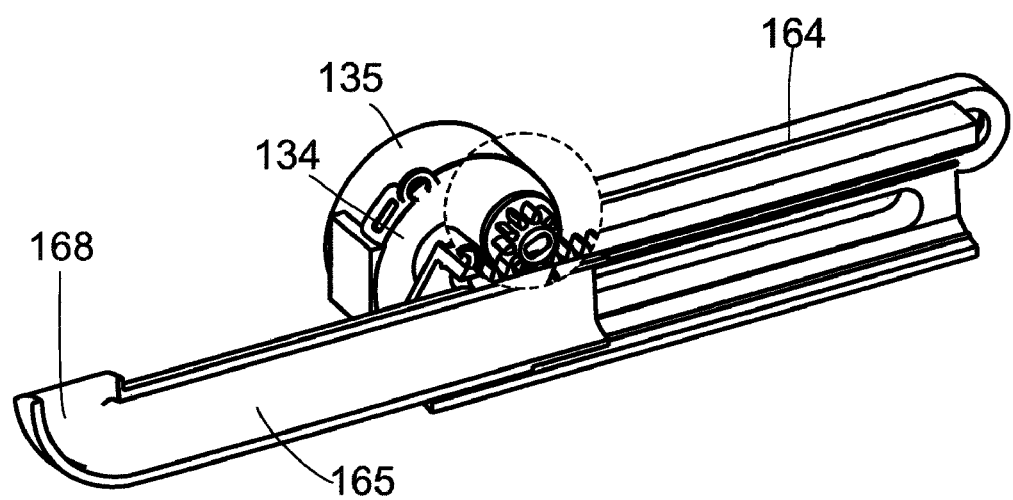
FIG. 7C is a cross-sectional view of the dryer assembly of FIG. 7A, showing a driving motor assembly used to move and extend the dryer assembly according to one embodiment of the invention.

FIG. 7A is a side perspective view of the spray canister device 100 installed next to a dynamic dryer and spray nozzle assembly, e.g., the wash and dry assembly 150 as shown, where a dryer wand 165 of a dryer assembly of the wash and dry assembly 150 is being extended out of a dryer housing 164 and ready to blow air or gases out of its front blower head. FIG. 7B is a side view of the dryer assembly, showing the dryer housing 164 of the dryer assembly and a driving motor assembly with a motor 134, a motor holder 135, a rack 146 and a slot element for moving the dryer assembly. FIG. 7C is a cross-sectional view of the dryer assembly of FIG. 7A, showing a driving motor assembly used to move and extend the dryer assembly according to one embodiment of the invention.

Referring back to FIG. 1, the wash and dry system may further includes one or more power switches or control units 340, 342 and 344 such that various motors and electric circuits contained within the system can be turned on for powering up the system and operating wash, clean, dry, protect and other functions of the wash and dry system. The control units can be positioned, in one example, on the top or the side of the system, and can be easily visible to a user. In one embodiment, the control unit 340 is a remote control unit. In addition, one or more power indicators can be positioned on the control units 340, 342 and 344 to indicate turning on of the electric power and proper functioning of the wash and clean system. In one example, a power indicator and the control unit 344 can be positioned at or near a front side of the system as exemplarily shown in FIG. 1.

In one aspect, the wash and clean system is connected to a power cord via a power connector. The power cord is adapted to connect to an electric outlet and provide electric power to power up the wash and dry system. In another aspect, the wash and dry system is connected to a battery power pack in order to conveniently power up the wash and dry system without the need to find an electric outlet.

In operation, once the electric power is turned on and the motors within the wash and dry system are adapted to deliver all desirable liquids (e.g., water and liquid from a water hose assembly via a water inlet, a cleaning or medication liquid solution from the medicine delivery assembly 190, and combinations thereof) from one or more channels therein to the spray nozzle assembly.

Figure 8:
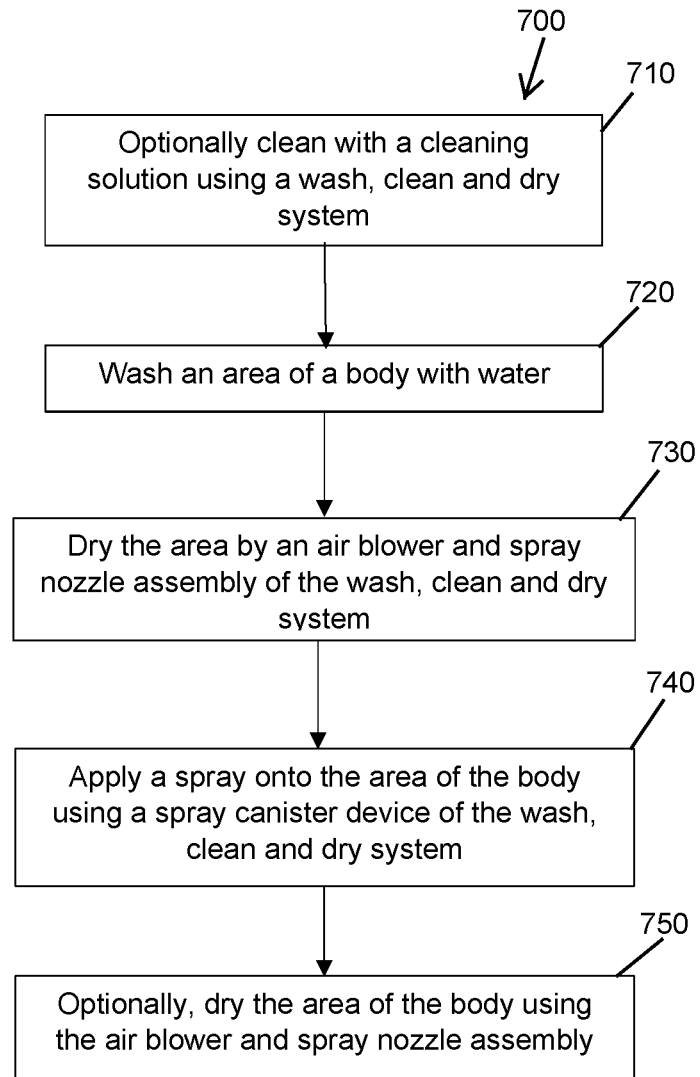
FIG. 8 illustrates a method of operating a wash and dry system with a removable spray canister device according to one or more embodiments of the invention.

FIG. 8 illustrates a method 700 of operating a wash and dry system with a removable spray canister device according to one or more embodiments of the invention. In one aspect, the method includes, optionally, at step 710 of cleaning the surface area of the subject using a cleaning solution sprayed from the wash and dry system.

In another aspect, the method includes positioning a wash and dry system near a surface area of a subject, where the wash and dry system includes a toilet seat assembly comprising a housing, a spray canister device inside the housing, and a spray nozzle assembly inside the housing. At step 720, the surface area of the subject is washed using the spray nozzle assembly, and at step 740, a spray delivered from an opening of the spray canister device is applied onto the surface area of the subject.

At step 730, the surface area of the subject is dried using a dryer assembly of the wash and dry system. In one example, drying the surface area is performed by the dryer assembly at high power prior to applying the spray delivered from the spray canister device. Optionally, at step 750, drying the surface area is performed by the dryer assembly at low power after applying the spray delivered from the spray canister device.

Further, the method may also include installing the spray canister device into the housing of the toilet seat assembly prior to using the wash and dry system. In one example, the spray canister device is installed by gripping a handle grip of the spray canister device and positioning the spray canister device into a cover of the housing of the toilet seat assembly. In another example, the spray canister device is installed by coupling a trigger bar of the spray canister device securely onto a delivery rack inside the housing of the toilet seat assembly.

In another embodiment, the method may further include shaking the spray canister device by moving the spray canister device inside the housing of the toilet seat assembly. In one aspect, shaking the spray canister device is performed prior to applying the spray delivered from the spray canister device.

In still another embodiment, the method may further include applying the spray by moving a canister element of the spray canister device against a sleeved cover element of the spray canister device along a delivery rack inside the housing of the toilet seat assembly.

In one embodiment, the removable sleeved cover element of the spray canister device includes a top cap portion, an opening, a sleeve portion, a handle grip, and a trigger bar. In another embodiment, the inner canister element includes a top outlet and a canister body. In still another embodiment, the canister body of the inner canister element is covered by a sleeved portion of the removable sleeved cover element and the top outlet is fitted to channels inside the top cap portion of the removable sleeved cover.

While the foregoing is directed to embodiments of the present invention, other and further embodiments of the invention may be devised without departing from the basic scope thereof, and the scope thereof is determined by the claims that follow.

What is claimed is:

1. An apparatus for storing a barrier material or medicament and spraying the barrier chemical or medicament onto a region of the human body, comprising:
   a toilet seat assembly comprising a seat, a seat cover, a seat body, and a compartment;
   a medicine delivery assembly operatively connected to the toilet seat assembly, the medicine delivery assembly configured to deliver the barrier chemical or medicament;
   a spray canister device operatively connected to the toilet seat assembly and configured to deliver the barrier material, wherein the spray canister device comprises a sleeved cover element and a canister element;
   a dryer assembly operatively connected to the toilet seat assembly inside in the compartment;
   a spray nozzle assembly operatively connected to the toilet seat assembly inside the compartment;
   a cover configured to extend over the spray canister device; and
   a plurality of control units operatively connected to the toilet seat assembly.

2. The apparatus of claim 1, wherein thespray canister device is positioned inside the compartment such that the spray device is removable or stationary.

3. The apparatus of claim 1, wherein the dryer assembly and the spray nozzle assembly are combined, thereby forming a dynamic washing and drying assembly.

4. The apparatus of claim 3, wherein the dynamic washing and drying assembly further comprises one or more nozzle units.

5. The apparatus of claim 1, wherein the spray canister device is operatively connected to a track.

6. The apparatus of claim 1, wherein the barrier chemical or medicament includes one or a combination of skin protectants, ointments, mineral oil, silicone fluids, dimethicone, cyclomethicone, petrolatum, cod liver oil, lanolin, zinc oxide, talc, calamine, kaolin, topical starch and allantoin, barrier materials, skin moisturizers, skin lotions, moisturizing creams, skin sealants, water, cleaning solutions, moisture barriers, a pharmaceutical formulation, and combinations thereof.

7. The apparatus of claim 1, wherein the spray nozzle assembly further comprises one or more steering mechanisms, and a driving motor being connected to one or more spray nozzle wands of the spray nozzle assembly and adapted for moving the one or more spray nozzle wands in a three-dimensional circular rotational motion.

8. The apparatus of claim 1, wherein the drying assembly further comprises:
a first driving motor operatively connected to one or more drying nozzle units, wherein the first driving motor is configured to move one or more retractable air blower wands in a retracting motion and an extending motion; and a second driving motor operatively connected to the one or more drying nozzle units, wherein the second driving motor is configured to move the one or more retractable air blower wands in three-dimensional circular rotational motion.

9. The apparatus of claim 1, wherein the medicine delivery assembly further comprises one or more medicine storage cartridges, wherein the medicine delivery assembly is adapted to deliver the medicament from one or more medicine storage cartridges.

10. The apparatus of claim 9, wherein the medicine delivery assembly is operatively coupled to a spray nozzle wand of the spray nozzle assembly.

11. A method of using an apparatus to deliver a barrier chemical or medicament to a region of a human body, the method comprising:
preparing a cleaning solution or a therapeutic solution containing the barrier chemical or medicament using the apparatus; washing an area of the region with water using the apparatus; and delivering the cleaning solution or the therapeutic solution to the region of the human body using the apparatus; wherein the apparatus comprises:
a toilet seat assembly comprising a seat, a seat cover, a seat body, a base housing unit, a base housing unit cover; a medicine delivery assembly; a spray canister device comprising a sleeved cover element and a canister element; a dryer assembly; a spray nozzle assembly; and one or more control units.

12. The method of claim 11, further comprising triggering a trigger bar of the sleeved cover element against the canister element, thereby moving a bottom portion of the canister element closer to an opening of the sleeved cover element.

13. An apparatus for storing a first liquid product and spraying the first liquid product onto a region of a human body, the apparatus comprising:
a toilet seat assembly including a base and a seat, the base having a base housing; a spray canister device configured to store the first liquid product therein; wherein the spray canister device is configured to be removably installed in a delivery track positioned in the base housing of the base; and wherein the spray canister device is configured to be moved along the delivery track between a retracted position and an extended position to deliver the first liquid product to the region.

14. The apparatus of claim 13, wherein the base housing includes a base housing cover pivotably coupled thereto, and wherein the spray canister device is configured to be installed in the delivery track through an aperture of the base housing covered by the base housing cover.

15. The apparatus of claim 13, further comprising a driving motor operatively coupled to the spray canister device, the driving motor configured to cause the spray canister device to move between the retracted position and the extended position along the delivery track.

16. The apparatus of claim 15, further comprising a control unit configured to cause operation of the motor upon receiving a user input.

17. The apparatus of claim 13, wherein the spray canister device further includes a canister element, a sleeved cover element, and a trigger bar, the trigger bar configured to be coupled to the delivery track in the base housing.

18. The apparatus of claim 17, wherein the spray canister device further includes a handle grip.

19. The apparatus of claim 17, wherein the trigger bar is configured to cause relative movement between the canister element and the sleeved cover element to spray the first liquid product.

20. The apparatus of claim 13, wherein the first liquid product includes one or a combination of skin protectants, ointments, mineral oil, silicone fluids, dimethicone, cyclomethicone, petrolatum, cod liver oil, lanolin, talc, calamine, kaolin, topical starch and allantoin, barrier materials, zinc oxide, skin moisturizers, skin lotions, moisturizing creams, skin sealants, water, cleaning solutions, moisture barriers, medicaments, and a pharmaceutical formulation.

* * * * *